(12) United States Patent
Tanabe

(10) Patent No.: US 7,344,502 B2
(45) Date of Patent: Mar. 18, 2008

(54) PULSE WAVE MEASURING APPARATUS OF HIGH MEASUREMENT ACCURACY

(75) Inventor: Kazuhisa Tanabe, Kyoto (JP)

(73) Assignee: Omron Healthcare Co., Ltd., Kyoto (JP)

(*) Notice: Subject to any disclaimer, the term of this patent is extended or adjusted under 35 U.S.C. 154(b) by 177 days.

(21) Appl. No.: 10/816,891

(22) Filed: Apr. 5, 2004

(65) Prior Publication Data

US 2004/0199080 A1 Oct. 7, 2004

(30) Foreign Application Priority Data

Apr. 4, 2003 (JP) ............................. 2003-101602

(51) Int. Cl.
*A61B 5/00* (2006.01)
(52) U.S. Cl. ...................................... 600/485; 600/501
(58) Field of Classification Search ................ 600/481, 600/485, 490, 492–494, 500
See application file for complete search history.

(56) References Cited

U.S. PATENT DOCUMENTS

| | | | | |
|---|---|---|---|---|
| 2,658,505 A | * | 11/1953 | Sheer | 600/500 |
| 3,880,145 A | | 4/1975 | Blick | |
| 4,269,193 A | * | 5/1981 | Eckerle | 600/485 |
| 4,561,447 A | * | 12/1985 | Kawamura et al. | 600/500 |
| 4,893,631 A | * | 1/1990 | Wenzel et al. | 600/485 |
| 5,065,765 A | | 11/1991 | Eckerle et al. | |
| 5,363,855 A | | 11/1994 | Drzewiecki et al. | |
| 5,381,797 A | * | 1/1995 | Pak et al. | 600/500 |
| 6,364,842 B1 | * | 4/2002 | Amano et al. | 600/485 |
| 6,612,993 B2 | * | 9/2003 | Narimatsu | 600/500 |

FOREIGN PATENT DOCUMENTS

| | | |
|---|---|---|
| JP | 2776961 | 5/1998 |
| JP | 2002-320594 | 11/2002 |

OTHER PUBLICATIONS

Chen et al., "Validation of Carotid Artery Tonometry as a Means of Estimating Augmentation Index of Ascending Aortic Pressure," Hypertension, vol. 27, 1996, pp. 168-175.
European Search Report dated Sep. 9, 2004, relating to EP Application No. 04007705.9.

\* cited by examiner

*Primary Examiner*—Charles A. Marmor, II
*Assistant Examiner*—Karen E. Toth
(74) *Attorney, Agent, or Firm*—Morrison & Foerster LLP

(57) ABSTRACT

A pulse wave measuring apparatus includes a pressure sensor having a plurality of sensor elements wider in width than the small sensor element required in conventional tonometry. On the basis of differences $\alpha$ and $\beta$ of an AI value based on a pulse wave signal from the sensor element right above an artery and AI values based on pulse wave signals from two sensor elements located at a predetermined distance from the sensor element right above the artery, $\alpha^2+\beta^2$ is obtained. An AI value correction is calculated using a regression formula with $\alpha^2+\beta^2$ as a correction parameter representing the distortion degree. Using this correction value, the AI based on a pulse wave signal from the sensor element located right above the artery is corrected.

9 Claims, 13 Drawing Sheets

AI ERROR GREAT

AI ERROR SMALL

PULSE WAVE MEASURING APPARATUS OF HIGH MEASUREMENT ACCURACY

BACKGROUND OF THE INVENTION

1. Field of the Invention

The present invention relates to a pulse wave measuring apparatus, particularly a pulse wave measuring apparatus of high measurement accuracy at low cost.

2. Description of the Background Art

Conventional pulse wave measuring apparatuses include the type measuring the pulse wave with a pressure sensor set right above an artery. It is extremely difficult to accurately position the pressure sensor right above an artery in such pulse wave measuring apparatuses. Technique of high level was required for the positioning of such pulse wave measuring apparatuses. There was also the problem that the reproducibility of measurement is poor since the positioning reproducibility is not good.

There is known a sphygmograph apparatus employing tonometry, directed to overcome the problem set forth above.

The mechanism of tonometry will be described with reference to FIG. 16. Referring to FIG. 16, the artery is pressed superficial of the body with a flat plate, whereby the artery is deformed to a leveled form. At the region right above the flat artery, the effect of blood vessel tension indicated by the dotted arrow in FIG. 16 on the pressure in the blood vessel is smallest since the blood vessel tension is balanced between the left and right sides. This means that the pressure measured by a sensor element smaller in size than the flat pressed region right above the leveled artery is consistent with the intra-arterial pressure. Thus, the intra-arterial waveform can be measured superficial of the body.

One type of a conventional pulse wave measuring apparatus employing tonometry has a plurality of small sensor elements aligned, as the pressure sensor positioned right above an artery to depress the contacting region for measurement of a pulse wave. The pulse wave is measured by the sensor element located right above the artery. Such a blood pressure monitor employing tonometry is disclosed in, for example, Japanese Patent No. 2776961.

Since the pulse wave measuring apparatus employing tonometry has a plurality of small sensor elements aligned, the possibility of any one of the sensor elements being located right above the artery is high. Therefore, positioning of the apparatus is facilitated. The positioning of a plurality of aligned sensor elements is disclosed in, for example, Japanese Patent Laying-Open No. 2002-320594, filed by the applicant of the present application prior to the filing of the present invention.

The pulse wave measuring apparatus employing tonometry set forth above must have a plurality of sensor elements as small as approximately 0.2-0.3 mm in width, for example, aligned. Accordingly, critical requirements such as high sensitivity and microfabrication must be satisfied. This necessitates the usage of a semiconductor silicon MEMS (Micro Electro Mechanical Systems) pressure sensor, resulting in an expensive sensor. Further, the complexity of electronic circuitry receiving the sensor signals will be increased since signals from many sensor elements are to be processed. There was a problem that the cost is increased.

If the aforementioned small sensor elements are not used in the pulse wave measuring apparatus directed to overcome the problem set forth above, the leveled region of an artery will become smaller than the width of the sensor element, leading to the problem of measurement error. This problem will be described in detail with reference to FIG. 17. FIG. 17 shows the AI (Augmentation Index), calculated based on the pulse waves measured by respective sensor elements of small size (0.2 mm in width) aligned on an artery. The AI is a parameter significantly affected by distortion in a sensor signal. This AI will be described in detail in the section of the embodiments of the present invention.

It is appreciated from FIG. 17 that the increase of an AI value representing the degree of sensor signal distortion becomes greater as a function of distance from the leveled region. This means that the degree of sensor signal distortion becomes larger. As shown in FIG. 16, this arises from that fact that, as located farther from the leveled region, the effect of the resultant force of the blood vessel tension on the pressure in the blood vessel will become greater due to the generation of blood vessel tension in a direction other than the direction parallel to the leveled region.

A larger width of the sensor element consequently allows a larger range of detection, leading to the possibility of a region other than the leveled region being included. As a result, the possibility of a region of high sensor signal distortion as shown in FIG. 17 being included in the range of detection will be increased. Thus, the possibility of measurement error caused by distortion in a sensor signal from a sensor element is high. Such a problem is similarly encountered, not only in the case where the sensor element is large in width, but also in the case where the pressurization force of the sensor element is insufficient, or when the sensor element is pressed back in response to a high intra-arterial pressure.

SUMMARY OF THE INVENTION

In view of the foregoing, an object of the present invention is to provide a low cost pulse wave measuring apparatus maintaining high measurement accuracy.

According to an aspect of the present invention, a pulse wave measuring apparatus includes a pressure pulse wave sensor with a plurality of sensor elements for detecting an intra-arterial pressure waveform superficial of a body, a select unit selecting a sensor element located right above an artery out of the plurality of sensor elements based on a sphygmographic waveform detected with the pressure pulse wave sensor, a sphygmographic waveform minutia value calculation unit calculating a minutia value using an amplitude value of a predetermined minutia based on the sphygmographic waveform detected with the selected sensor element, a distortion degree calculation unit calculating the difference in the distortion degree of sphygmographic waveforms detected by respective sensor elements based on the sphygmographic waveform detected with the selected sensor element and the sphygmographic waveform detected with at least one sensor element located at a predetermined distance from the selected sensor element, and an amplitude value correction unit correcting the amplitude value of the predetermined minutia using the calculated distortion degree difference.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
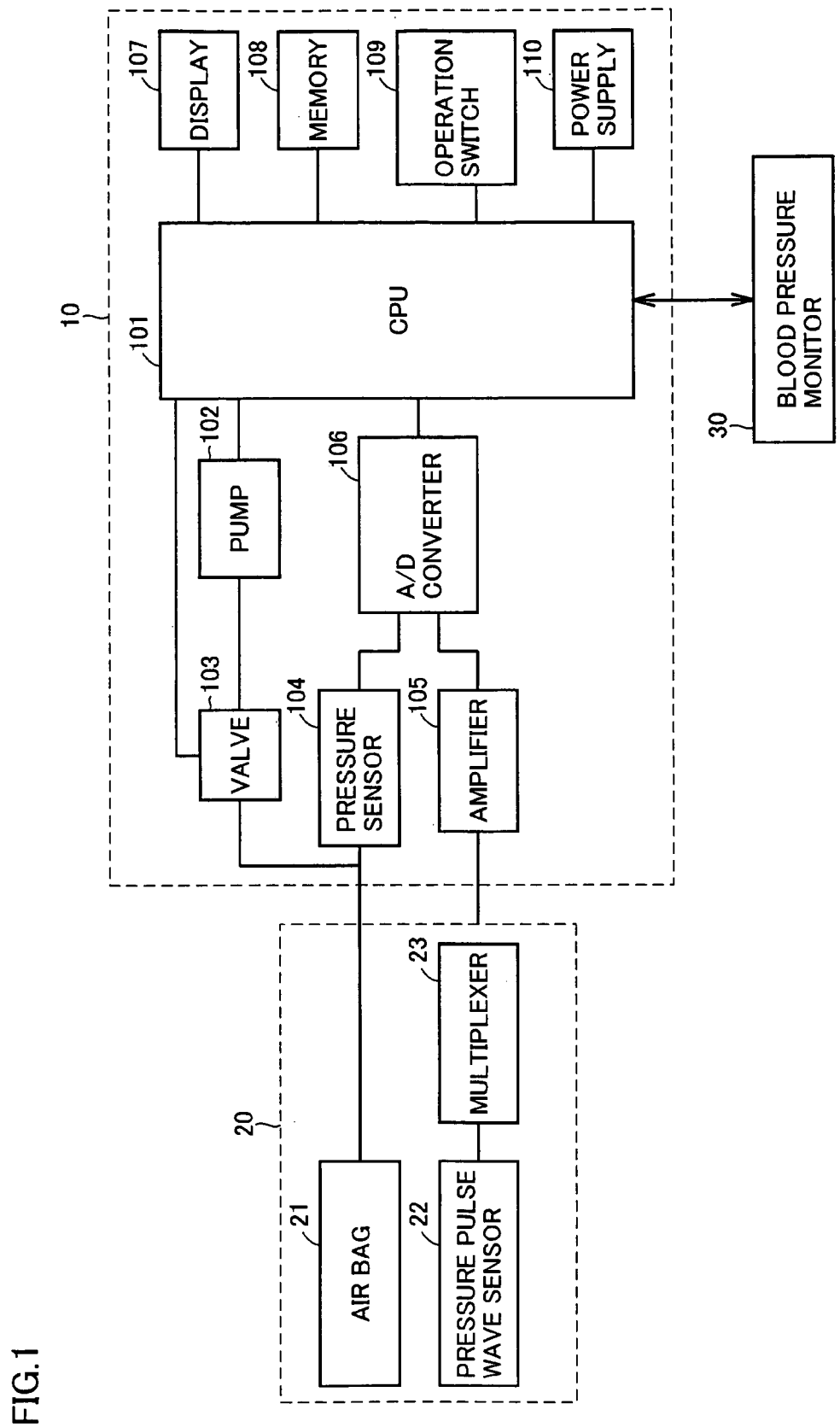
FIG. 1 specifically shows an example of a structure of a pulse wave measuring apparatus in accordance with an embodiment.

Embodiments of the present invention will be described hereinafter with reference to the drawings. In the following description, the same components and elements have the same reference character allotted. Their designation and function are identical. Therefore, detailed description thereof will not be repeated.

Referring to FIG. 1, a pulse wave measuring apparatus according to the present embodiment is mainly formed of a main unit 10 and a sensor unit 20. Main unit 10 is connected to an external blood pressure monitor 30. It is assumed that the connection between main unit 10 and blood pressure monitor 30 includes those through a dedicated cable, a communication line, or the like, or a non-contact radio communication. In FIG. 1, the sphygmograph apparatus is implemented with main unit 10 having communication capability, and is capable of measuring blood pressure, as necessary, in cooperation with blood pressure monitor 30. It will be understood that such description is merely exemplary, and the sphygmograph apparatus may directly include a blood pressure monitor 30 to allow measurement of blood pressure.

Main unit 10 includes a CPU (Central Processing Unit) 101, powered by a power supply 110 to operate. CPU 101 establishes access to a storage device such as a memory 108 to read out and execute a program for overall control of the pulse wave measuring apparatus.

CPU 101 receives an operation signal set by a user through an operation switch 109 to carry out control processing of the entire pulse wave measuring apparatus based on the operation signal. Specifically, CPU 101 responds to an operation signal input through operation switch 109 to transmit control signals to a pump 102, a valve 103 and blood pressure monitor 30, and then receives a measurement result from blood pressure monitor 30.

Pump 102 and valve 103 function to inflate or deflate an air bag 21 included in sensor unit 20. A pressure sensor 104 detects the pressure (cuff pressure) in air bag 21 to provide a pressure signal to an A/D converter 106.

A pressure pulse wave sensor 22 in sensor unit 20 is configured with a plurality of sensor elements aligned at a predetermined interval, and is pressed against the measurement site of a subject such as the wrist of the subject through the pressure of air bag 21. Under this status, sensor unit 20 detects the pulse wave of the subject. Pressure pulse wave sensor 22 applies the detected pulse wave signal to a multiplexer 23 for the channel of each sensor element. The pulse wave signal is applied from multiplexer 23 to an amplifier 105.

Amplifier 105 amplifies the pulse wave signal of each channel from multiplexer 23 to a predetermined level. The amplified signal is applied to A/D converter 106.

A/D converter 106 converts into digital information the pressure signal that is an analog signal from pressure sensor 104 and the pulse wave signal that is an analog signal from amplifier 105. The digital information is applied to CPU 101.

CPU 101 provides a digital signal to a display 107 and/or memory 108.

Pressure pulse wave sensor 22 of the pulse wave measuring apparatus of the present embodiment shown in FIG. 1 is formed of sensor elements, each of a size larger than the sensor size required in general tonometry. The pulse wave measuring apparatus of the present embodiment is characterized in that the distortion of a signal measured with such a sensor element located right above an artery is corrected.

The processing carried out in the pulse wave measuring apparatus of the present embodiment will be described with reference to the flow chart of FIG. 2. The process shown in the flow chart of FIG. 2 is realized by CPU 101 of the pulse wave measuring apparatus, establishing access to a storage device such as memory 108 to read out and execute a program.

Figure 2:
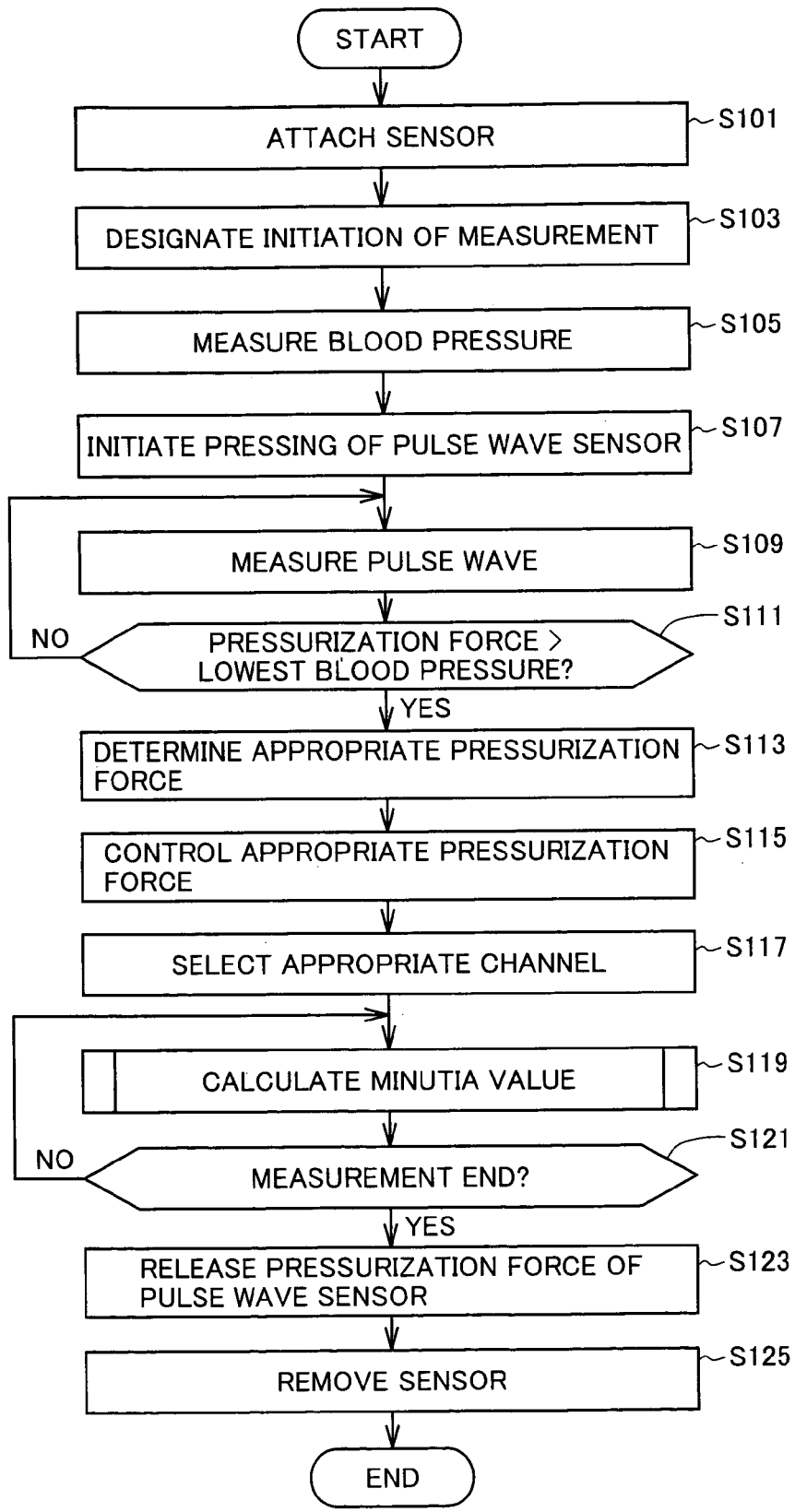
FIG. 2 is a flow chart of the process at the pulse wave measuring apparatus of the present embodiment.

Referring to FIG. 2, to initiate measurement of pulse waves, sensor unit 20 is attached to a measurement site (S101) such as the wrist of a subject by means of a belt not shown. Then, CPU 101 sends a control signal to blood pressure monitor 30 to designate initiation of blood pressure measurement (S103). When the blood pressure of the subject is measured though blood pressure monitor 30 (S105), CPU 101 proceeds to initiate measurement of a pulse wave. Specifically, CPU 101 transmits control signals so as to open valve 103 and apply pressure to pump 102 such that the pressure in air bag 21 attains a predetermined pressure gradient while detecting the pressure in air bag 21 applied from pressure sensor 104 via A/D converter 106, whereby the pressure in air bag 21 is increased to initiate pressurization of pressure pulse wave sensor 22 (S107).

Each sensor element constituting pressure pulse wave sensor 22 is pressed against the measurement site of the subject to respectively detect the beat of the artery (S109). To establish an appropriate pressurization force at that stage, CPU 101 increases the pressure in air bag 21 to a level higher than the minimal blood pressure of the subject (YES at S111), and then determines the appropriate pressurization force (S113).

The way of determining whether or not the pressure in air bag 21 has exceeded the minimal blood pressure at step S111 is not limited to that described in the present invention. For example, determination can be made that the pressure in air bag 21 has exceeded the minimal blood pressure if there is a leveled region immediately preceding the rising point of the pulse wave detected by pressure pulse wave sensor 22.

Further, the way of defining the appropriate pressurization force at step S113 is also not limited to that described in the present invention. Various known ways can be employed. For example, the region exhibiting small change in the pulse wave amplitude with respect to change in pressure in a range of pressurization force below the minimal blood pressure can be defined as the appropriate pressurization force.

CPU 101 controls valve 103 and pump 102 so that the pressure in air bag 21 corresponds to the appropriate pressurization force defined at step S113 (S115). Specifically, when the pressure in air bag 21 arrives at the appropriate pressurization force level, CPU 101 closes valve 103 to maintain that appropriate pressurization force. Any deviation of the pressurization force from the appropriate level due to air leakage or body movement can be sensed through CPU 101 by monitoring the pressure value applied from pressure sensor 104 via A/D converter 106. In response to detection of such deviation, valve 103 and pump 102 are controlled adaptively to maintain the appropriate pressurization force.

When the pressurization force of pressure pulse wave sensor 22 attains the appropriate level, CPU 101 determines the sensor element with a sensor detection region in which the region located right above the artery of the subject is included (S117). The way of determining the sensor element of step S117 is not limited to that described in the present invention. For example, the method disclosed in Japanese Patent Laying-Open No. 2002-320594, filed by the applicant of the present application prior to the filing of the present invention, can be used.

Then, CPU 101 calculates the minutia value based on the pulse wave measured by the sensor element determined at step S117 (S119). This process will be described in detail afterwards with reference to a flow chart. CPU 101 repeats the process of calculating a minutia value of step S119 until the measurement end condition is established (YES at S121). The condition to end the measurement of step S121 may be an elapse of a preset predetermined time, or an interruption designated by the user.

When measurement of pulse wave ends, CPU 101 opens valve 103 to release the pressure of pressure sensor 104, and operates pump 102 to deflate air bag 21 (S123). Upon release of the pressure of pressure sensor 104, the user removes sensor unit 20 from the measurement site (S125). Thus, the series of pulse wave measurement process ends.

The minutia value calculation process executed at step S119 will be described here. In the present embodiment, the AI (Augmentation Index) value is taken as the minutia value.

As used herein, AI is a well known index, which is an indexed version of the minutia value reflecting the intensity of pulse wave reflection corresponding to arteriosclerosis of central blood vessel. It is said that AI is an effective index for an early diagnosis of circulatory disorder, and is known to exhibit a behavior different from that of blood pressure. AI is calculated from the measured pulse wave by CPU 101 at the above-described step S119. In the case where the pulse wave measuring apparatus is connected to an information processor such as a computer not shown and the measurement information is processed by the same, the AI may be calculated by the CPU in the information processor.

Figure 3:
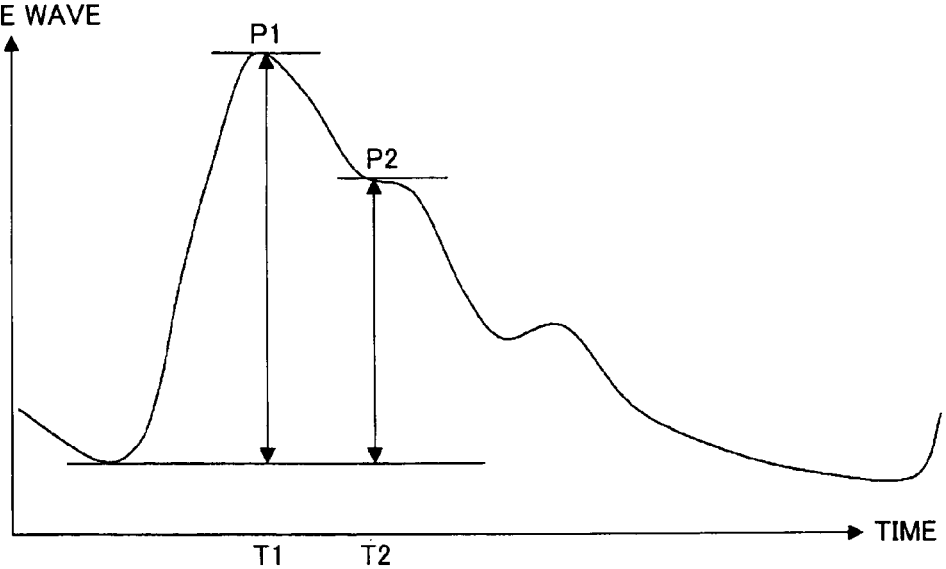
FIGS. 3 and 4 show specific examples of change in a pulse wave over time.
Figure 4:
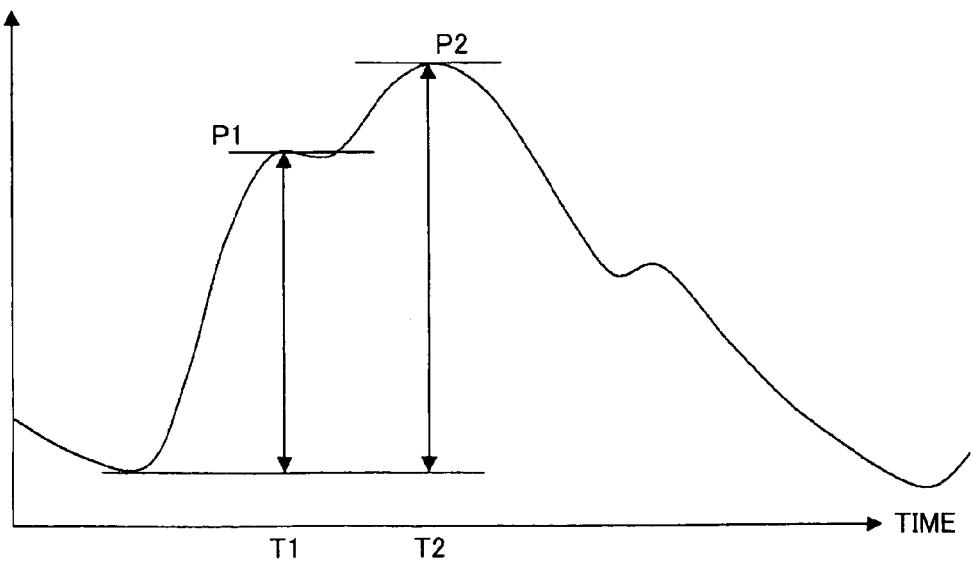

FIGS. 3 and 4 show specific examples of change in the measured pulse wave over time. For example, the AI value is obtained as AI=P1/P2 (or AI (%)=(P2−P1)/P1×100) when the pulse wave shown in FIG. 3 is measured. The AI value is obtained as AI=P1/P2 (or AI (%)=(P2−P1)/P2×100) when the pulse wave shown in FIG. 4 is measured. Level P1 at time T1 indicates the value by an ejection wave of blood caused by a heart beat, whereas level P2 at time T2 indicates the value by a reflected wave of the ejection wave caused by a heart beat. The intensity and appearance time of this reflected wave based on the rising point of the ejection wave change, corresponding to the hardening of the blood vessel. One way of determining P1 and P2 is to apply an arithmetic operation such as differentiation on the sphygmographic waveform. In general, a younger subject exhibits the relationship of level P2<level P1, as shown in FIG. 3, whereas an older subject exhibits the relationship of level P2>level P1, as shown in FIG. 4. This is attributed to the advancement of hardening of the inner wall of a blood vein (arteriosclerosis) as the age of a subject becomes higher. The ejection wave cannot be absorbed sufficiently at the wall of the blood vessel, so that reflection of a high level will detected within a short period of time.

In accordance with the measurement of a pulse wave based on tonometry, the pulse wave must be detected with a sensor element of a width (approximately 0.2 mm) smaller than the leveled region of an artery. If the width of the sensor element is larger than the leveled region of the artery, the pressure in the artery measured by the sensor element and the sensor signal will not exhibit linearity, leading to generation of distortion.

Figure 5:
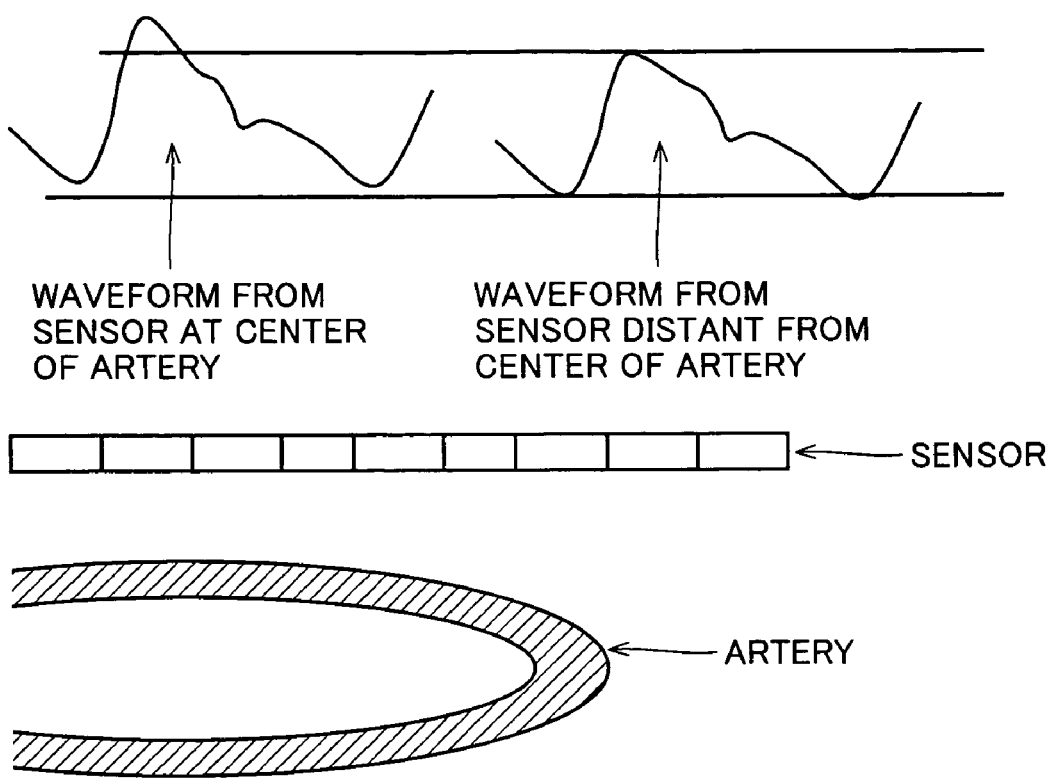
FIG. 5 represents the relationship between the position of a sensor element with respect to an artery and the waveform of a pulse wave measured by the sensor element.
Figure 16:
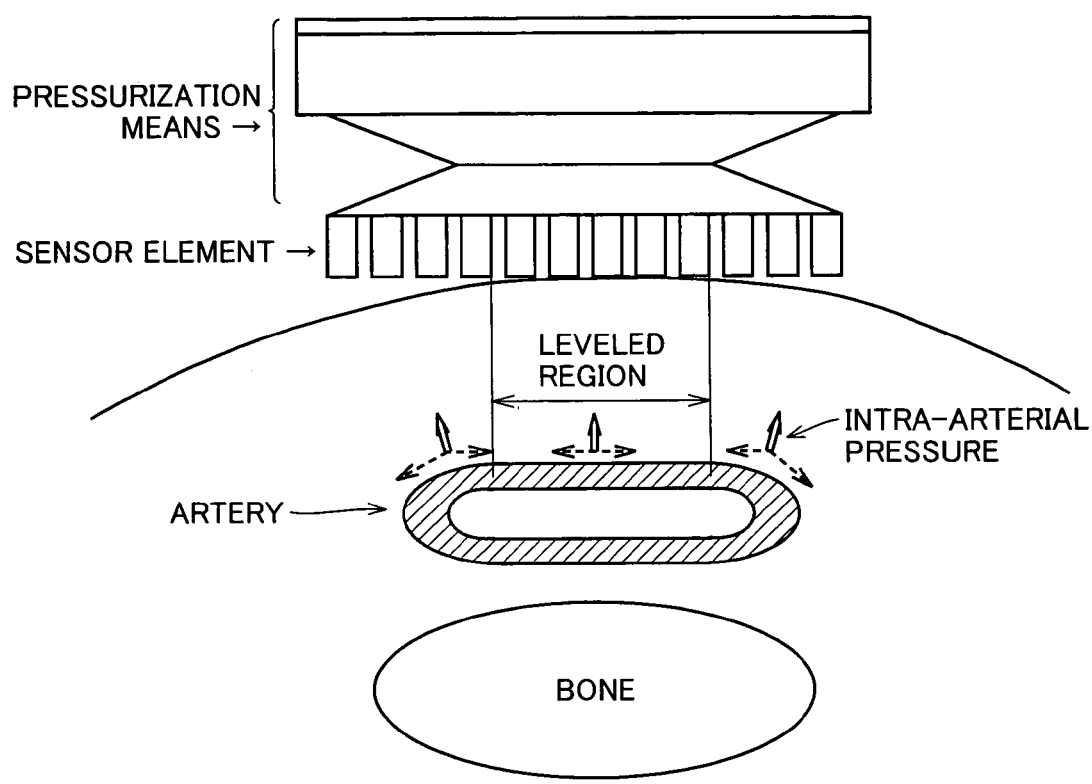
FIG. 16 is a diagram to describe the principle of tonometry.

It is appreciated from FIG. 5 showing the relationship between the position of a sensor element with respect to the artery and the waveform of the pulse wave measured by the sensor element that the amplitude of the pulse wave is generally apt to be low when measured by a sensor element located distant from the center region of the artery that is not completely leveled than when measured by a sensor element located right above the artery that is leveled. This arises from the fact that the pulse wave detected by a sensor element is influenced by the tension of the blood vessel generated at a site distant from the center of the artery (refer to FIG. 16).

Figure 6:
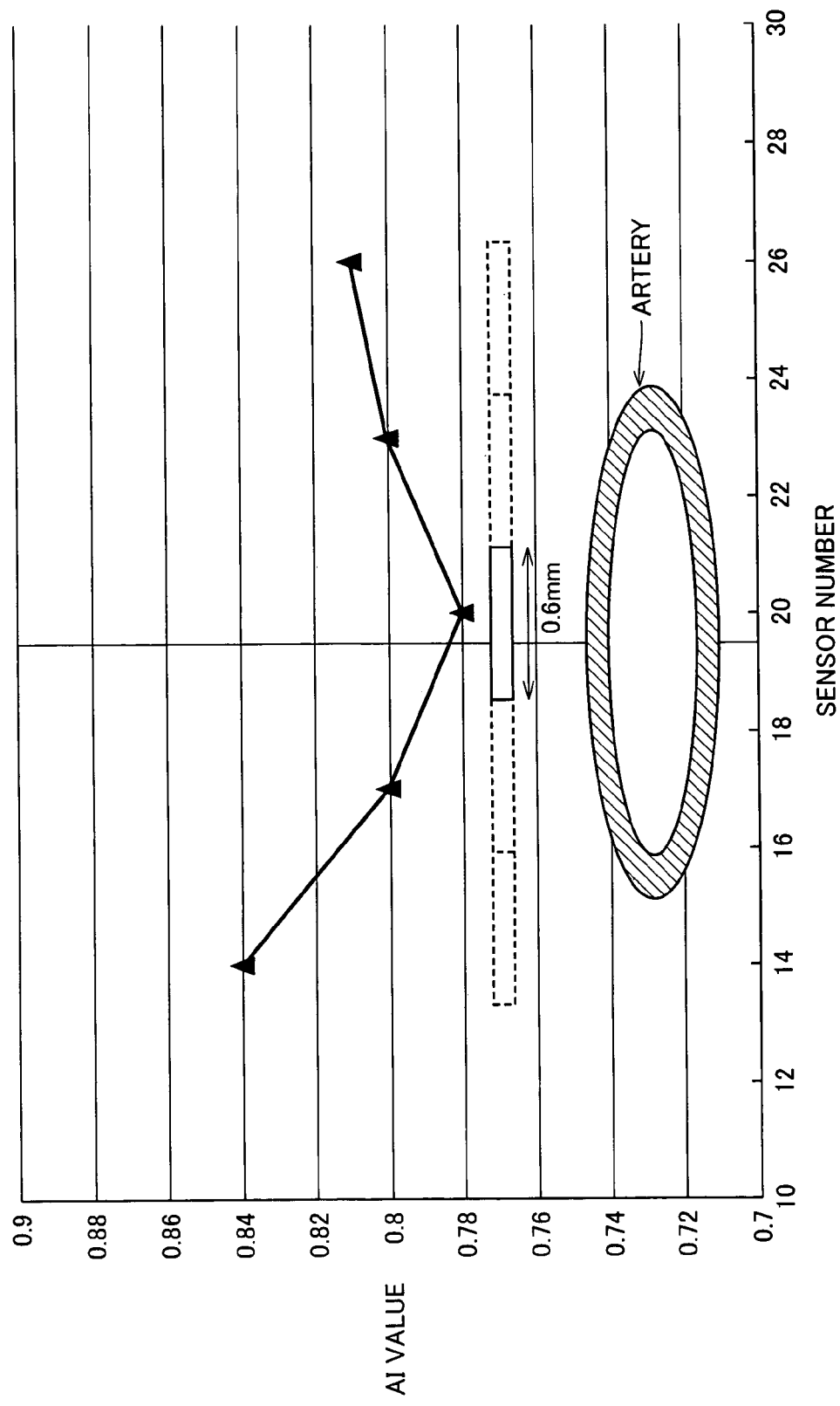
FIG. 6 shows AI values obtained based on pulse waves measured by respective sensor elements of 0.6 mm in width, aligned on an artery.
Figure 7:
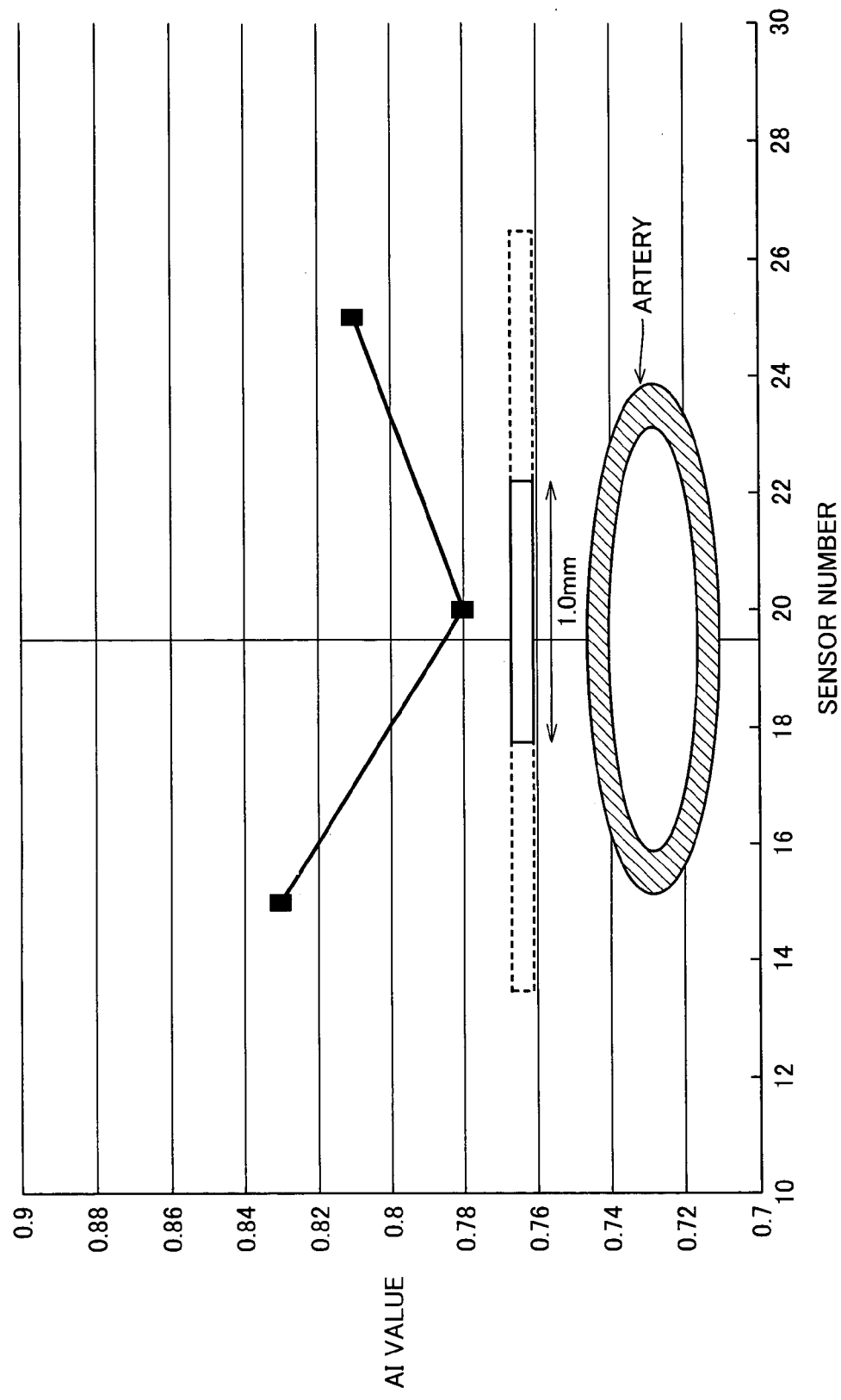
FIG. 7 shows AI values obtained based on pulse waves measured by respective sensor elements of 1.0 mm in width, aligned on an artery.
Figure 17:
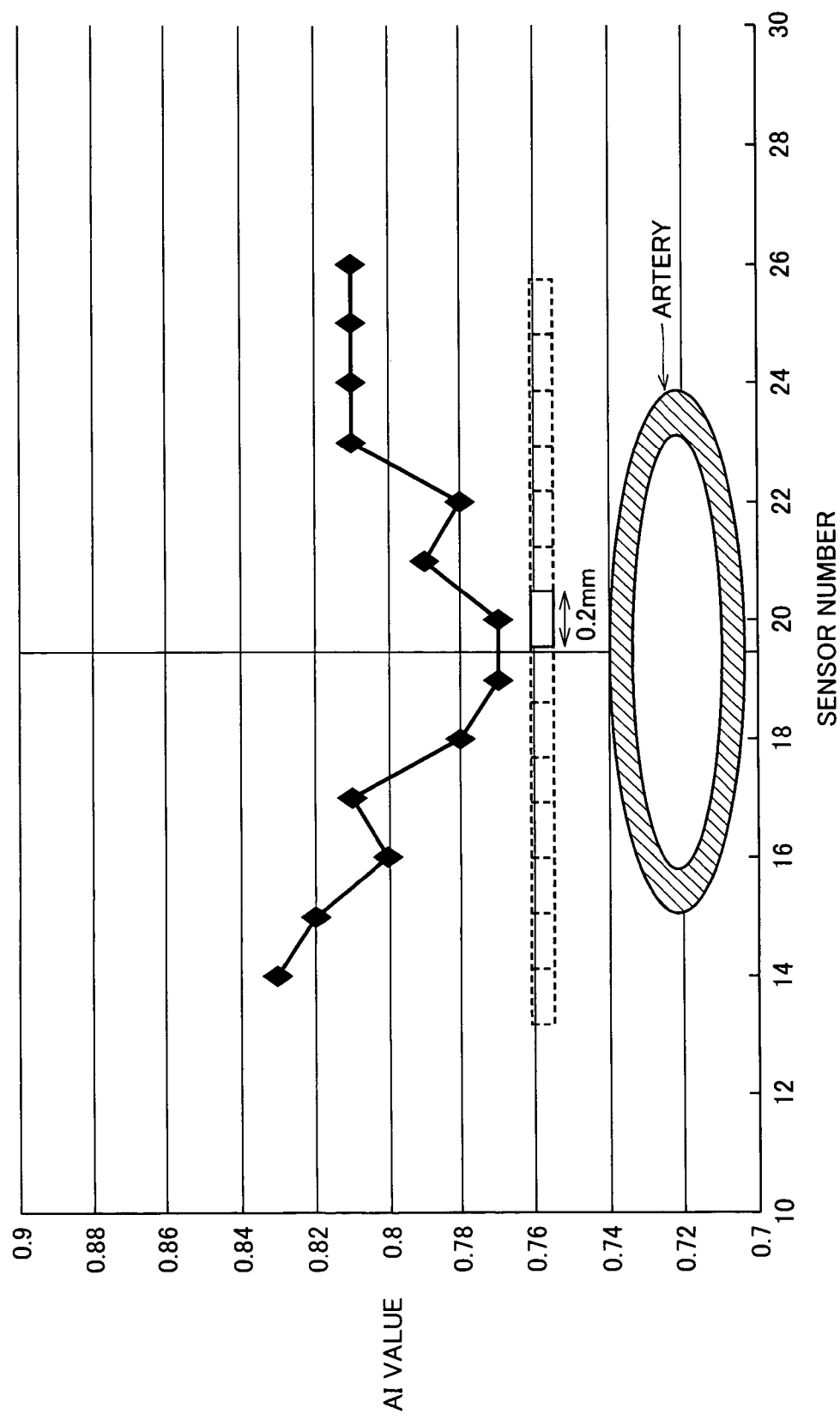
FIG. 17 represents AI values obtained by pulse waves measured by respective small sensor elements aligned on an artery.

This distortion in a sensor signal is significantly perceptible by the calculated AI value. FIGS. 6 and 7 show AI values obtained from pulse waves measured by respective sensor elements aligned on the artery, the former corresponding to measurement using a sensor element of 0.6 mm in width and the latter a sensor element of 1.0 mm in width. FIGS. 6 and 7 as well as FIG. 17 showing AI values obtained from pulse waves measured with a sensor element of 0.2 mm in width exhibit the tendency of obtaining a higher AI value even if it was based on pulse waves measured by a sensor element whose center point is located on the same position on the artery. This is because, as the width of the sensor element becomes larger, a pulse wave is measured from a range of an artery including a position distant from the center area of the artery that is leveled. In other words, FIGS. 6, 7 and 17 exhibit the tendency of greater error in the AI value as the width of the sensor element becomes larger.

Figure 8:
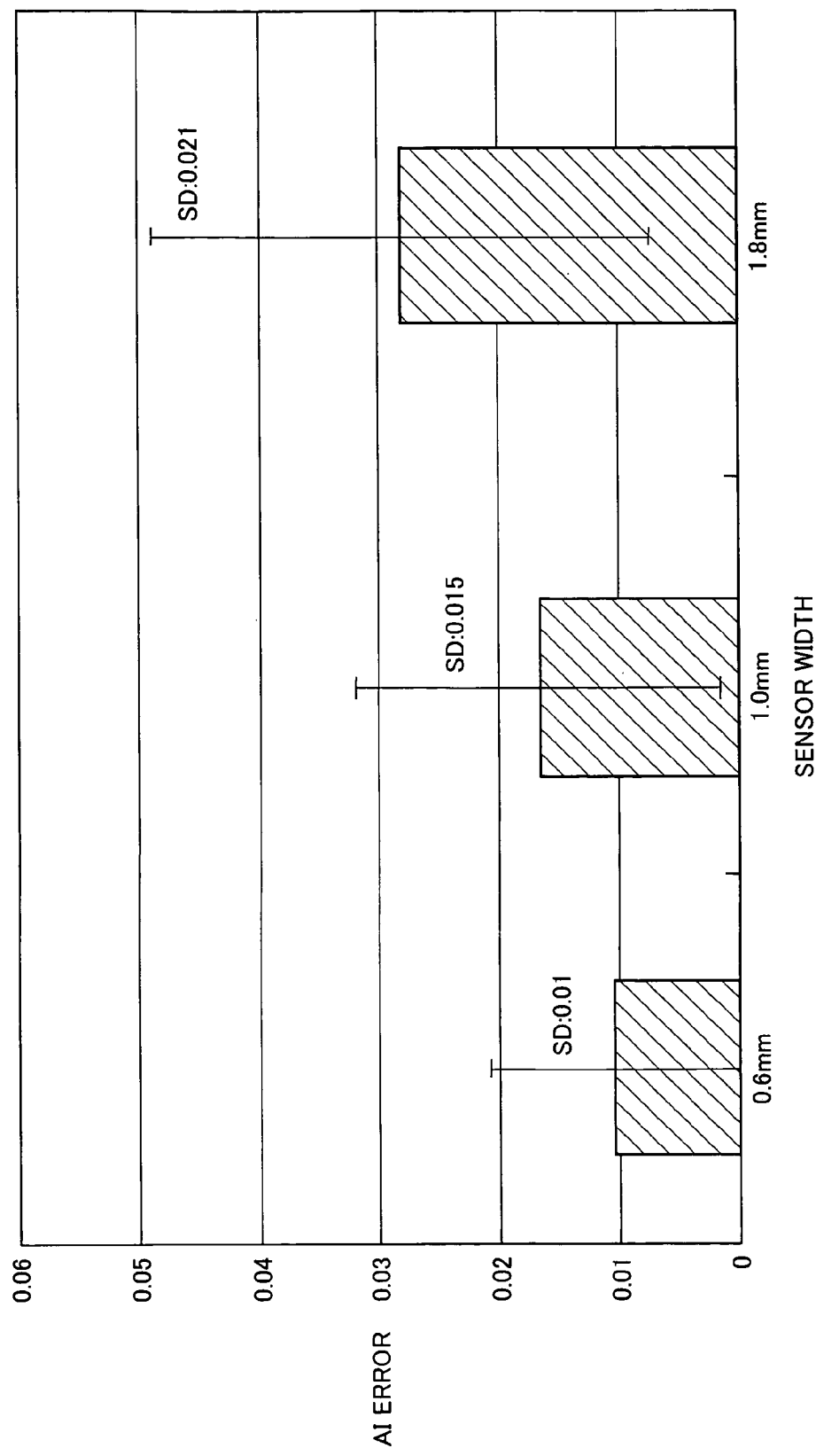
FIG. 8 shows the relationship between the sensor element width and AI value error.

This relationship between the sensor element width and AI value error is shown in FIG. 8. Referring to FIG. 8, the distortion of a sensor signal becomes greater as a function of a larger sensor element width, leading to greater error in the AI value. It is appreciated that the standard deviation (SD) indicating dispersion in AI error is also greater.

It is also appreciated from FIGS. 6 and 7 that the sensor signal distortion is greater as the position of the sensor element becomes more distant from the region right above the artery, or as the position of the sensor element becomes more distant from the leveled region of the artery. In other words, the AI value calculated based on a sensor signal from each sensor element also reflects the degree of distortion in the sensor signal from each sensor element.

In view of the foregoing, the pulse wave measuring apparatus of the present embodiment corrects the distortion in the sensor signal from the sensor element located right above the artery based on the difference between the distortion of a sensor signal from a sensor element with a sensor detection region in which the area right above the artery is included (for the sake of simplification, referred to as "sensor element right above the artery" hereinafter) and the distortion of a sensor signal from a sensor element located at a predetermined distance from the sensor element right above the artery, in the minutia value calculation process of step S19 in FIG. 2.

Figure 9:
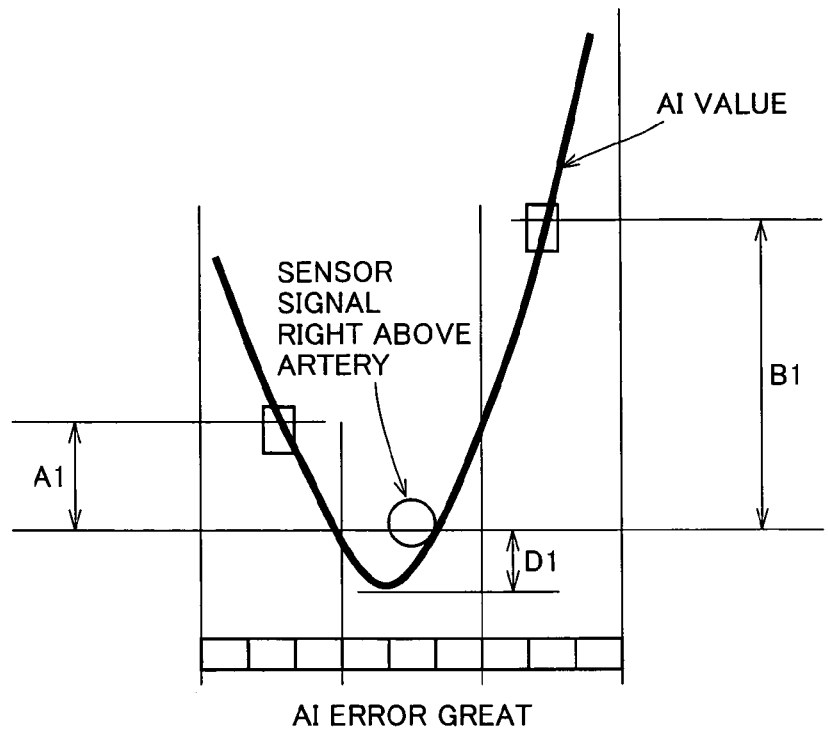
FIG. 9 schematically shows the distribution of AI values when the sensor element width is large.
Figure 10:
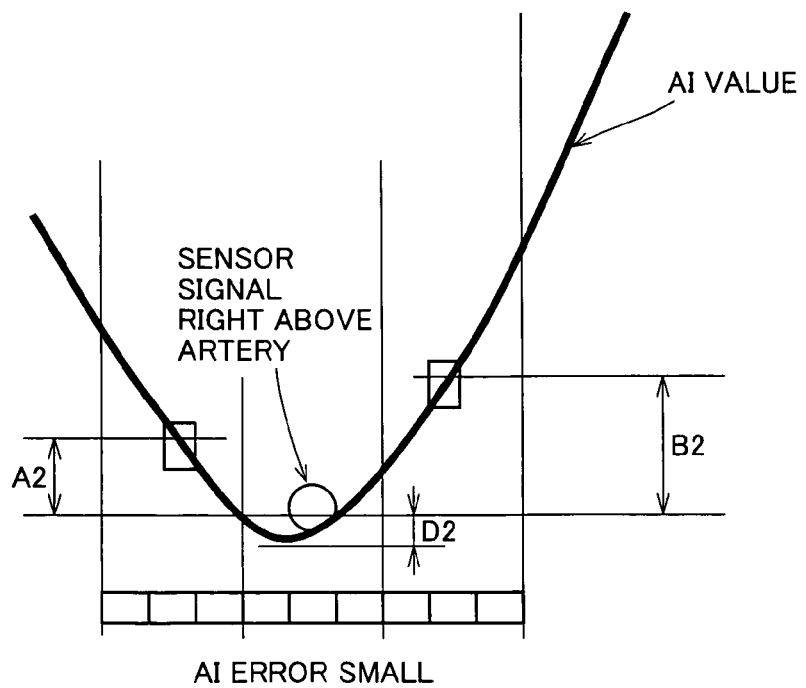
FIG. 10 schematically shows the distribution of AI values when the sensor element width is small.

The distribution of AI values calculated by sensor signals from respective sensor elements when the sensor element width is large and small is shown in FIGS. 9 and 10, respectively. The mechanism of the aforementioned correction will be described hereinafter.

The distortion degree of a sensor signal is defined from an AI value calculated based on a sensor signal from a sensor element right above an artery, and an AI value calculated based on a sensor signal from a sensor element located at a predetermined distance from the sensor element right above the artery. In other words, the distortion degree of a sensor signal of respective cases is defined from the difference between an AI value based on a sensor signal from a sensor element right above an artery and an AI value based on a sensor signal from a sensor element located at a predetermined distance from the sensor element right above the artery (A1 and B1 of FIG. 9, and A2 and B2 of FIG. 10). A1 and A2 are generically referred to as "A" and B1 and B2 are generically referred to as "B" hereinafter. The method of defining the degree of distortion is not limited to that described in the present invention. For example, it may be defined with a coefficient (A+B), or a coefficient ($A^2+B^2$).

On the basis of the definition of distortion degree set forth above, the sensor signal distortion degree is great when the sensor element width is large relative to the diameter of an artery, as shown in FIG. 9. In the event of a great sensor signal distortion degree, the leveled region of the artery is small relative to the sensor element detection region, so that it is assumed that the distortion of the sensor signal from the sensor element right above the artery is also great. In FIG. 9, the distortion of a sensor signal from a sensor element right above the artery is indicated by D1. On the other hand, when the sensor element width is smaller than the width in FIG. 9, the distortion degree D2 of a sensor signal is smaller than D1, as shown in FIG. 10. In the event of a small sensor signal distortion degree, the leveled region of the artery is large relative to the sensor element detection region, so that it is assumed that the distortion of the sensor signal from the sensor element right above the artery is also small. Thus, the AI value calculated from a pulse wave measured by the sensor located right above the artery can be corrected taking advantage of this distortion degree.

Figure 11:
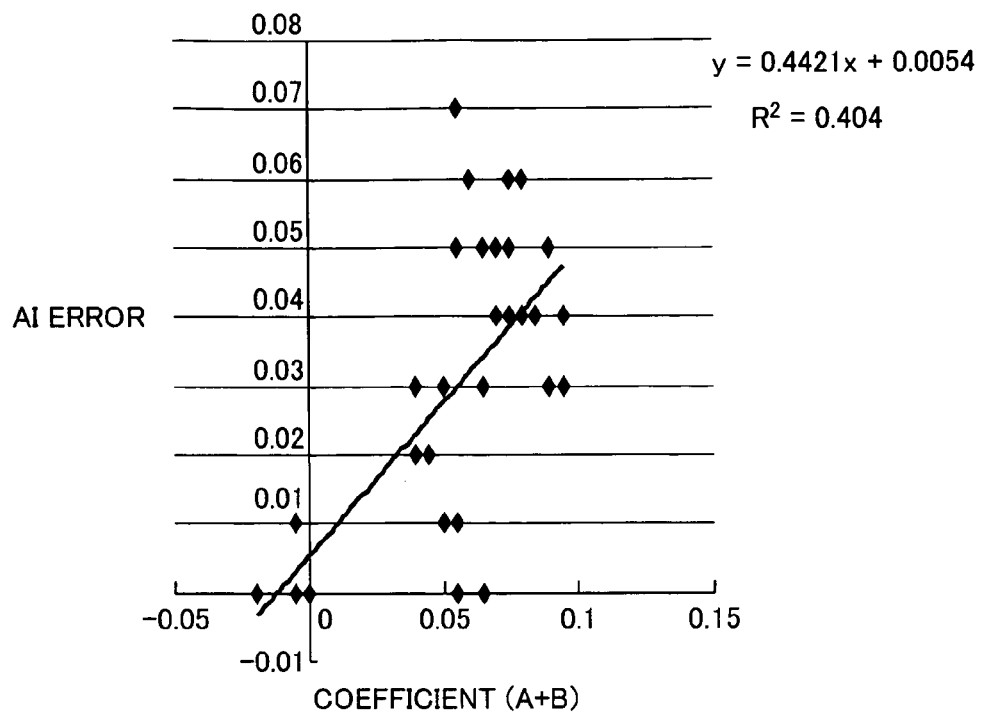
FIG. 11 shows the relationship between the sum of the difference of AI values that are parameters representing the distortion degree and the error of AI values calculated from the pulse wave measured with the sensor element located right above the artery.
Figure 12:
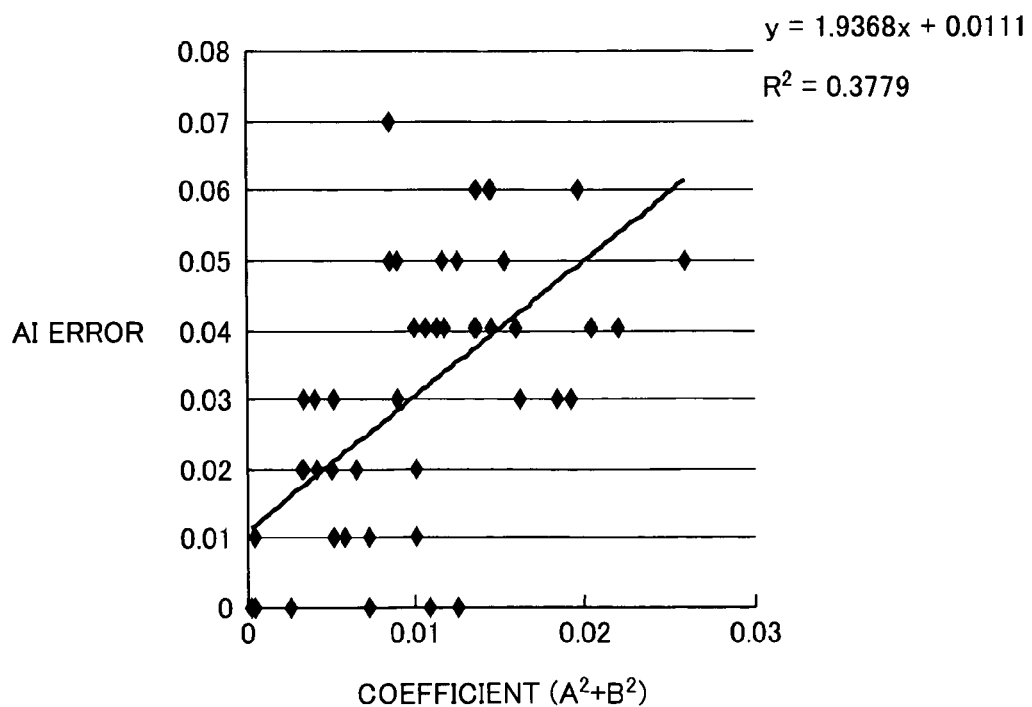
FIG. 12 represents the relationship between the sum of squares of the difference of AI values that are parameters representing the distortion degree and the error of AI values calculated from the pulse wave measured by the sensor element located right above the artery.

The relationship between a parameter representing the distortion degree and error in the AI value calculated from a pulse wave measured by the sensor right above the artery in the event of measuring a pulse wave with a sensor element of 1.8 mm in width is shown in FIGS. 11 and 12. FIG. 11 corresponds to the case where the sum of the difference of AI values (the aforementioned coefficient (A+B)) is employed as the parameter representing the distortion degree. FIG. 12 corresponds to the case where the sum of squares of the difference of AI values (the aforementioned coefficient ($A^2+B^2$)) is employed as the parameter representing the distortion degree.

It is appreciated from FIGS. 11 and 12 that the parameter representing the distortion degree correlates with the error in the AI value calculated from a pulse wave measured with a sensor element right above the artery. Using a regression formula obtained from these relations, the error in AI value can be estimated. The present pulse wave measuring apparatus is characterized in that an AI value absent of error is calculated in the minutia value calculation process of step S119 utilizing the above-described correlating relationship.

The minutia value calculation process of step S119 will be described with reference to the flow chart of FIG. 13. First, CPU 101 calculates an AI value AIc based on a pulse wave signal input through the channel relevant to the sensor element right above the artery, determined at step S117 (S201). Also, AI values AIa and AIb are calculated based on pulse wave signals input through channels relevant to two sensor elements located at a predetermined distance from the sensor element right above the artery.

Following definition of $\alpha$=AIa−AIc, and $\beta$=AIb−AIc, CPU 101 calculates $\alpha$ and $\beta$ to obtain $\alpha^2+\beta^2$ (S203). This corresponds to the method of using the sum of squares of the difference between AI values as the parameter representing the distortion degree, shown in FIG. 12.

Using the AI value correction calculation equation Y=NX+M that is a regression formula with $\alpha^2+\beta^2$ calculated at step S203 as the correction parameter representing distortion degree, the AI value correction value ($\Delta$AI) is calculated (S205). As used herein, N and M are predetermined coefficients.

The calculation of (AIc−$\Delta$AI) is carried out using the AI value correction value ($\Delta$AI) calculated at step S205 to correct AI value AIc obtained from the pulse wave measured with the sensor element right above the artery determined at step S117 (S207). The corrected AI value is shown at display 107 (S209).

Thus, the minutia value calculation process ends, and control returns to the main routine of FIG. 2.

Figure 14:
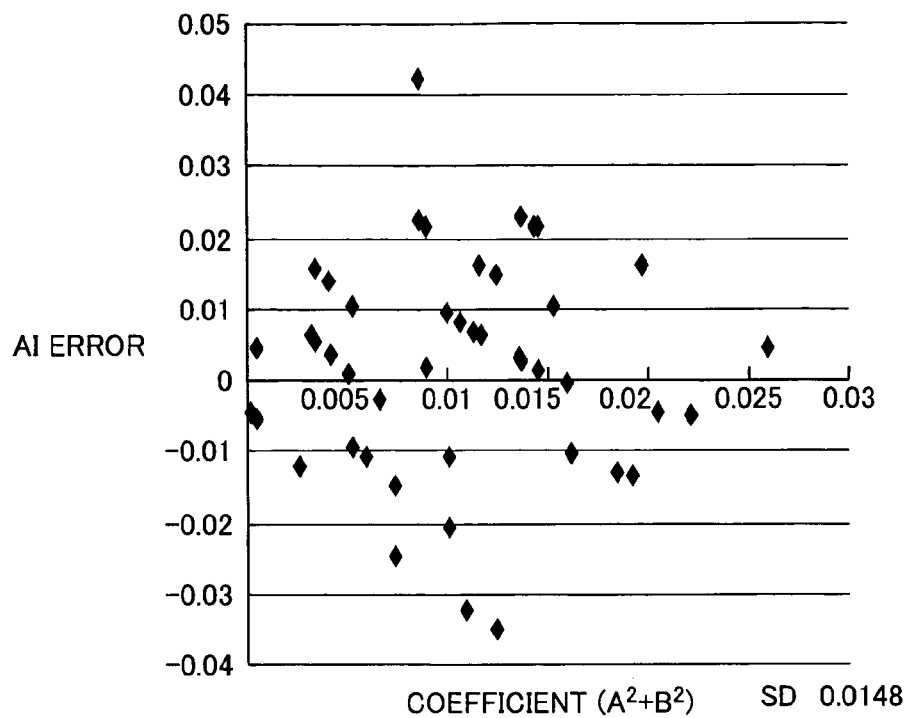
FIGS. 14 and 15 show the result of correction of the AI value.

By taking advantage of the difference between the distortion of a sensor signal from a sensor element right above an artery and the distortion of a sensor signal from a sensor element located at a predetermined distance from the sensor element right above the artery to correct the AI value calculated based on the waveform measured with the sensor element right above the artery in the present pulse wave measuring apparatus, the AI value obtained from the pulse wave measured by the sensor element right above the artery is corrected, leading to the result shown in FIG. 14. It is appreciated from FIG. 14 that the standard deviation SD representing dispersion in AI error is approximately 0.015, showing improvement from the standard deviation value SD of 0.021 in FIG. 8 prior to correction.

The minutia value calculation process of step S119 is not limited to the method of using the sum of squares of the difference in AI values as the parameter representing the distortion degree. Alternatively, the sum of difference between AI values specifically shown in FIG. 11 may be used. Specifically, $\alpha+\beta$ is calculated instead of $\alpha^2+\beta^2$ at step S203 to obtain an AI value correction (ΔAI) using the AI value correction calculation equation Y=NX+M that is a regression formula with α+β as the correction parameter representing the distortion degree at step S205.

Figure 15:
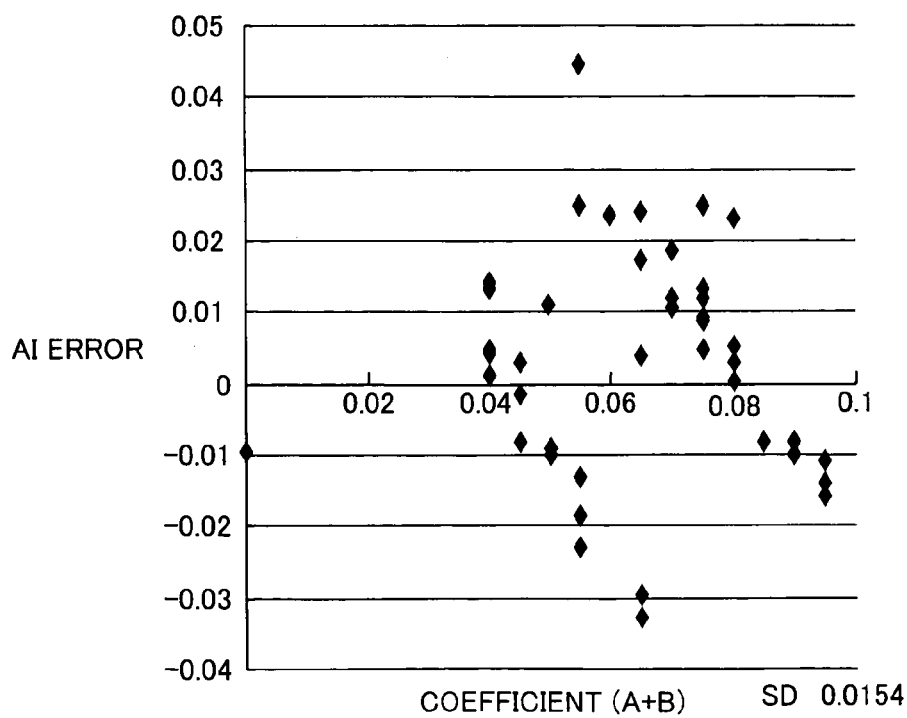

Similarly, the AI value obtained from the pulse wave measured with a sensor element right above the artery is corrected, leading to the result as shown in FIG. 15. Specifically, the standard deviation SD representing dispersion in AI error is reduced to approximately 0.015 in FIG. 15, which is an improvement from the previous SD (0.021) in FIG. 8 prior to correction.

Figure 13:
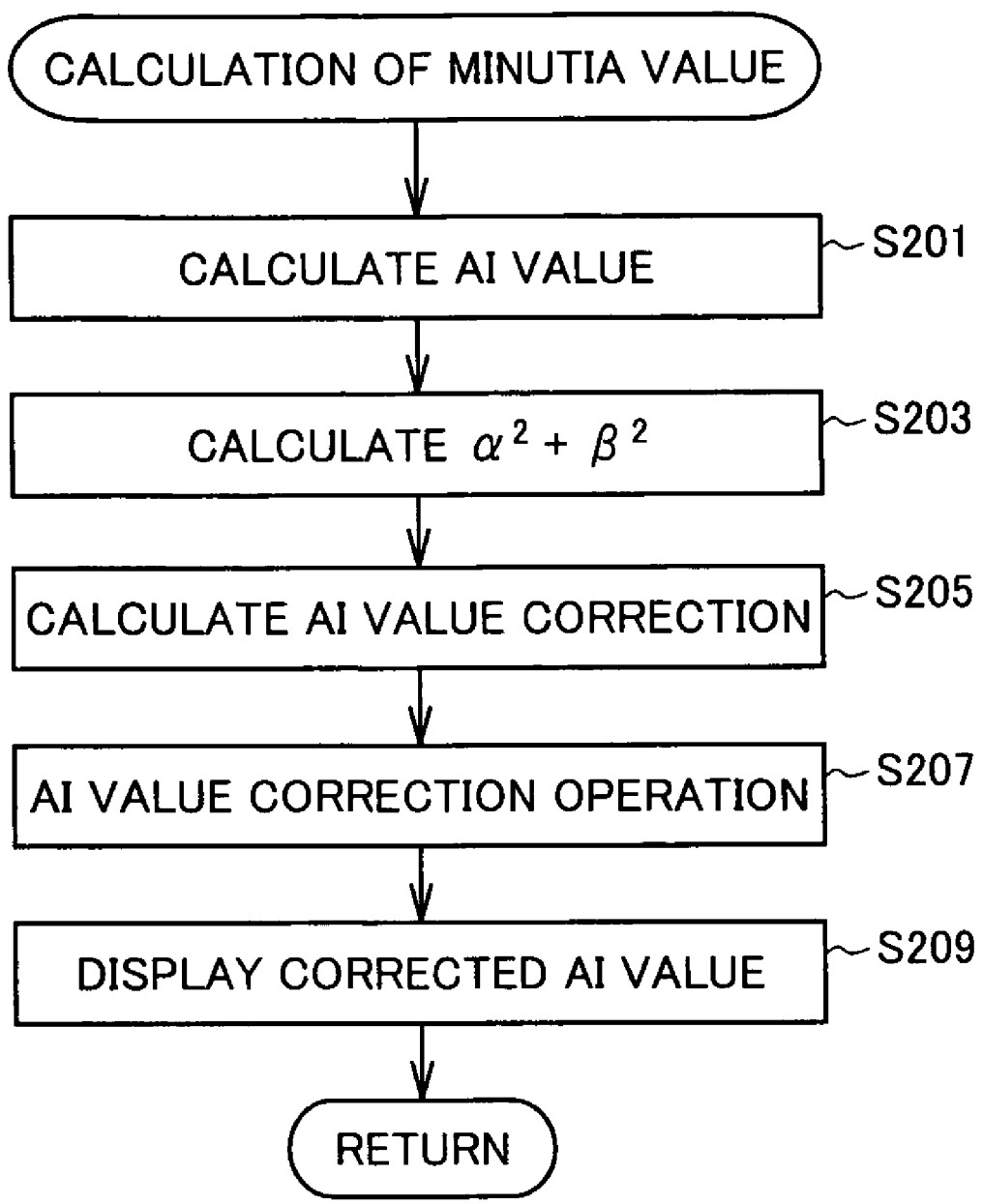
FIG. 13 is a flow chart of a minutia value calculation process of step S119.

The process shown in FIG. 13 corresponds to the case of a calculation (correction) process using pulse wave signals from two sensor elements as the sensor element located at a predetermined distance from the sensor element right above the artery. The number of sensor elements used is not limited to two. One or more than two sensor elements may be used.

It is to be noted that the present invention is not limited to the usage of AI as the minutia value. A similar advantage can be achieved by using, for example, the ratio of an area of one period of a pulse wave to the area starting from the rising point of a pulse wave to the dicrotic notch (can be used for cardiac function).

The above embodiment was described in which the correlation relation is used such as the sum of squares or the sum of differences between AI values which are minutia values as the parameter representing the distortion degree. A similar advantage can be achieved by using other correlation relationships as the parameter representing the distortion degree. As the first example thereof, pulse waveforms measured with respective sensor elements are normalized in one same phase, and then pulse wave height values in another same phase can be used. More specifically, the sphygmographic waveforms measured by respective sensor elements are normalized at the dicrotic notch, and the pulse wave height values of respective sensor elements at another time phase are obtained. The ratio of the pulse wave height value obtained from a pulse wave measured with the sensor element right above the artery to the pulse wave height value obtained from a pulse wave measured with a sensor element located at a predetermined distance from the sensor element right above the artery can be used as the parameter representing the distortion degree.

Alternatively, sphygmographic waveforms measured by respective sensor elements are normalized at the peak time phase, and pulse wave height values in another time phase can be used. Then, in a similar manner, the ratio of the pulse wave height value obtained from a pulse wave measured with the sensor element right above the artery to the pulse wave height value obtained from a pulse wave measured with a sensor element located at a predetermined distance from the sensor element right above the artery can be used as the parameter representing the distortion degree.

As the second specific example, pulse waveforms measured by respective sensor elements are normalized at the peak time phase, and each area obtained from pulse waveforms subjected to normalization can be used. The ratio of the above-described area obtained from a pulse wave measured with the sensor element right above the artery to the above-described area obtained from a pulse wave measured with a sensor element located at a predetermined distance from the sensor element right above the artery can be used as the parameter representing the distortion degree.

As the third specific example, each time width crossing the threshold value of a predetermined ratio after pulse waveforms measured with respective sensor elements are normalized at the peak time phase can be used. Specifically, pulse waveforms measured with respective sensor elements are normalized at the peak time phase. Taking the value lower than the peak by a predetermined pulse wave height as the threshold value for each waveform subjected to normalization, the time interval between two points crossing the threshold value for the pulse waveforms measured with respective sensor elements is obtained. The ratio of the above-described time width obtained from the pulse wave measured with the sensor element right above the artery to the above-described time width obtained from a pulse wave measured with a sensor element located at a predetermined distance from the sensor element right above the artery can be used as the parameter representing the distortion degree.

As the fourth specific example, the area ratio of the area preceding and succeeding the time phase of the dicrotic notch for pulse waveforms measured with respective sensor elements can be used. Specifically, an area α preceding the time phase of the dicrotic notch and an area β subsequent that time phase (right side) are obtained for pulse waveforms measured with respective sensor elements. Then, the area ratio α/β for each waveform is obtained. The ratio of the above-described area ratio obtained from the pulse wave measured with the sensor element right above the artery to the above-described area ratio obtained from a pulse wave measured with a sensor element located at a predetermined distance from the sensor element right above the artery can be used as the parameter representing the distortion degree.

As the fifth specific example, pulse waveforms measured with respective sensor elements are normalized at the area of the same pulse beat, and the maximum pulse wave height value of the normalized waveform can be used. The ratio of the above-described maximum pulse wave height value obtained from the pulse wave measured with the sensor element right above the artery to the above-described maximum pulse wave height value obtained from a pulse wave measured with a sensor element located at a predetermined distance from the sensor element right above the artery can be used as the parameter representing the distortion degree.

As the sixth specific example, the amplitude of pulse waveforms measured with respective sensor elements can be used. The ratio of the amplitude of the pulse wave measured with the sensor element right above the artery to the amplitude of a pulse wave measured with a sensor element located at a predetermined distance from the sensor element right above the artery can be used as the parameter representing the distortion degree.

Furthermore, the parameter representing distortion degree is not limited to the above-described sum of difference or sum of squares of difference of the minutia value calculated from the pulse waveform measured with the sensor element right above the artery and the minutia value calculated from the pulse waveform measured with a sensor element located at a predetermined distance from the sensor element right above the artery, as well as the ratios set forth above. It may be a correlation coefficient between the pulse waveform measured with the sensor element right above the artery and the pulse waveform measured with sensor elements located at a predetermined distance from the sensor element right above the artery.

Such parameters representing distortion degree can be used likewise to obtain a measured result of high accuracy with little dispersion in the minutia value.

In the pulse wave measuring apparatus of the present invention, the accuracy of AI that is the minutia value can be ensured even if the pulse wave is measured using a sensor element of a size larger than that of the small sensor element generally required in the tonometry system. Accordingly, the critical requirement of the working dimension of the sensor element, the sensor sensitivity and the like can be alleviated. The range of selection of pressure sensing methods that conventionally had to rely on semiconductor processing technology can be increased to allow reduction in cost. In other words, the pulse wave measuring apparatus of the present invention is not limited to the usage of pressure sensors obtained by processing expensive semiconductor silicon through MEMS (Micro Electro Mechanical Systems) that had to be used in a conventional pulse wave measuring apparatus employing tonometry. Other sensors using piezoelectric ceramic, piezoelectric polymer, thin metal film strain gauge, or the like can be used to allow reduction in cost.

Since the size of the sensor can be increased in the pulse wave measuring apparatus of the present invention, the number of sensor elements required can be reduced for an equal range of sensing pressure corresponding to that of the tonometry system having a plurality of small sensor elements aligned. Accordingly, the complexity of electronic circuitry receiving a sensor signal can be reduced to allow reduction in cost.

Furthermore, the larger sensor size in the pulse wave measuring apparatus of the present invention allows the effect of noise to be suppressed more than in the case of using conventional small sensor elements.

The minutia value calculation (correction) method of the pulse wave measuring apparatus set forth above can be provided as a program. Such a program can be stored in a computer-readable recording medium such as a flexible disc, CD-ROM (Compact Disc-Read Only Memory), ROM (Read Only Memory), RAM (Random Access Memory) or memory card associated with a computer to be provided as a program product. Alternatively, the program can be recorded in a recording medium such as a hard disk incorporated in a computer to be provided as a program. Furthermore, the program can be provided by downloading through a network.

The presented program product is installed in the program storage unit such as a hard disk for execution. The program product includes the program itself, and the recording medium in which the program is recorded.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A pulse wave measuring apparatus comprising:
  a pressure pulse wave sensor including a plurality of sensor elements, detecting an intra-arterial pressure waveform superficial of a body,
  a select unit selecting a selected sensor element located right above an artery out of said plurality of sensor elements based on a sphygmographic waveform detected with said pressure pulse wave sensor,
  a sphygmographic waveform value calculation unit calculating a characteristic value from the sphygmographic waveform detected with said selected sensor element,
  a distortion degree calculation unit calculating difference in distortion degree of sphygmographic waveforms detected with respective said sensor elements, based on a sphygmographic waveform detected with said selected sensor element and a sphygmographic waveform detected with at least one sensor element located at a predetermined distance from said selected sensor element, and
  an amplitude value correction unit correcting an amplitude value using said calculated difference in distortion degree,
  wherein said characteristic value includes an AI (Augmentation Index) value.

2. The pulse wave measuring apparatus according to claim 1, wherein said difference in distortion degree calculated at said distortion degree calculation unit is a sum of a difference between an AI value calculated from a sphygmographic waveform detected with said selected sensor element and an AI value calculated from a sphygmographic waveform detected with said at least one sensor element located at a predetermined distance from said selected sensor element at said sphygmographic waveform value calculation unit.

3. The pulse wave measuring apparatus according to claim 1, wherein said difference in distortion degree calculated at said distortion degree calculation unit is a sum of squares of a difference between an AI value calculated from a sphygmographic waveform detected with said selected sensor element and an AI value calculated from a sphygmographic waveform detected with said at least one sensor element located at a predetermined distance from said selected sensor element at said sphygmographic waveform value calculation unit.

4. A pulse wave measuring apparatus comprising:
  a pressure pulse wave sensor including a plurality of sensor elements, detecting an intra-arterial pressure waveform superficial of a body,
  a select unit selecting a selected sensor element located right above an artery out of said plurality of sensor elements based on a sphygmographic waveform detected with said pressure pulse wave sensor,
  a sphygmographic waveform value calculation unit calculating a characteristic value from the sphygmographic waveform detected with said selected sensor element,
  a distortion degree calculation unit calculating difference in distortion degree of sphygmographic waveforms detected with respective said sensor elements, based on a sphygmographic waveform detected with said selected sensor element and a sphygmographic waveform detected with at least one sensor element located at a predetermined distance from said selected sensor element, and
  an amplitude value correction unit correcting an amplitude value using said calculated difference in distortion degree,
  wherein said distortion degree calculation unit normalizes at a same phase a sphygmographic waveform detected with said selected sensor element and a sphygmographic waveform detected with said at least one sensor element located at a predetermined distance from said selected sensor element, and then calculates a ratio of a pulse wave height value of a sphygmographic waveform detected with said selected sensor element to a pulse wave height value of a sphygmographic waveform detected with said at least one sensor element located at a predetermined distance from said selected sensor element at a same phase other than said same phase, as said difference in distortion degree.

5. A pulse wave measuring apparatus comprising:
a pressure pulse wave sensor including a plurality of sensor elements, detecting an intra-arterial pressure waveform superficial of a body,
a select unit selecting a selected sensor element located right above an artery out of said plurality of sensor elements based on a sphygmographic waveform detected with said pressure pulse wave sensor,
a sphygmographic waveform value calculation unit calculating a characteristic value from the sphygmographic waveform detected with said selected sensor element,
a distortion degree calculation unit calculating difference in distortion degree of sphygmographic waveforms detected with respective said sensor elements, based on a sphygmographic waveform detected with said selected sensor element and a sphygmographic waveform detected with at least one sensor element located at a predetermined distance from said selected sensor element, and
an amplitude value correction unit correcting an amplitude value using said calculated difference in distortion degree,
wherein said distortion degree calculation unit normalizes a sphygmographic waveform detected with said selected sensor element and a sphygmographic waveform detected with said at least one sensor element located at a predetermined distance from said selected sensor element at a peak time phase, and then calculates a ratio of an area of said normalized sphygmographic waveform detected with said selected sensor element to an area of said normalized sphygmographic waveform detected with said at least one sensor element located at a predetermined distance from said selected sensor element, as said difference in distortion degree.

6. A pulse wave measuring apparatus comprising:
a pressure pulse wave sensor including a plurality of sensor elements, detecting an intra-arterial pressure waveform superficial of a body,
a select unit selecting a selected sensor element located right above an artery out of said plurality of sensor elements based on a sphygmographic waveform detected with said pressure pulse wave sensor,
a sphygmographic waveform value calculation unit calculating a characteristic value from the sphygmographic waveform detected with said selected sensor element,
a distortion degree calculation unit calculating difference in distortion degree of sphygmographic waveforms detected with respective said sensor elements, based on a sphygmographic waveform detected with said selected sensor element and a sphygmographic waveform detected with at least one sensor element located at a predetermined distance from said selected sensor element, and
an amplitude value correction unit correcting an amplitude value using said calculated difference in distortion degree,
wherein said distortion degree calculation unit normalizes a sphygmographic waveform detected with said selected sensor element and a sphygmographic waveform detected with said at least one sensor element located at a predetermined distance from said selected sensor element at a peak time phase, and then calculates a ratio of a time width of said normalized sphygmographic waveform detected with said selected sensor element crossing a threshold value of a predetermined ratio to a time width of said normalized sphygmographic waveform detected with said at least one sensor element located at a predetermined distance from said selected sensor element crossing said sensor element threshold value, as said difference in distortion degree.

7. A pulse wave measuring apparatus comprising:
a pressure pulse wave sensor including a plurality of sensor elements, detecting an intra-arterial pressure waveform superficial of a body,
a select unit selecting a selected sensor element located right above an artery out of said plurality of sensor elements based on a sphygmographic waveform detected with said pressure pulse wave sensor,
a sphygmographic waveform value calculation unit calculating a characteristic value from the sphygmographic waveform detected with said selected sensor element,
a distortion degree calculation unit calculating difference in distortion degree of sphygmographic waveforms detected with respective said sensor elements, based on a sphygmographic waveform detected with said selected sensor element and a sphygmographic waveform detected with at least one sensor element located at a predetermined distance from said selected sensor element, and
an amplitude value correction unit correcting an amplitude value using said calculated difference in distortion degree,
wherein said distortion degree calculation unit calculates a ratio of area ratios of a sphygmographic waveform detected with said selected sensor element, preceding and succeeding a time phase corresponding to a dicrotic notch in one beat to area ratios of a sphygmographic waveform detected with said at least one sensor element at a predetermined distance from said selected sensor element, preceding and succeeding said time phase, as said difference in distortion degree.

8. A pulse wave measuring apparatus comprising:
a pressure pulse wave sensor including a plurality of sensor elements, detecting an intra-arterial pressure waveform superficial of a body,
a select unit selecting a selected sensor element located right above an artery out of said plurality of sensor elements based on a sphygmographic waveform detected with said pressure pulse wave sensor,
a sphygmographic waveform value calculation unit calculating a characteristic value from the sphygmographic waveform detected with said selected sensor element,
a distortion degree calculation unit calculating difference in distortion degree of sphygmographic waveforms detected with respective said sensor elements, based on a sphygmographic waveform detected with said selected sensor element and a sphygmographic waveform detected with at least one sensor element located at a predetermined distance from said selected sensor element, and
an amplitude value correction unit correcting an amplitude value using said calculated difference in distortion degree,
wherein said distortion degree calculation unit normalizes a sphygmographic waveform detected with said selected sensor element and a sphygmographic waveform detected with said at least one sensor element located at a predetermined distance from said selected sensor element at an area of a same beat, and then calculates a ratio of a maximum pulse wave height value of said normalized sphygmographic waveform detected with said selected sensor element to a maximum pulse wave height value of said normalized sphygmographic waveform detected with said at least one sensor element located at a predetermined distance from said selected element, as said difference in distortion degree.

9. A pulse wave measuring apparatus comprising:

a pressure pulse wave sensor including a plurality of sensor elements, detecting an intra-arterial pressure waveform superficial of a body, a select unit selecting a selected sensor element located right above an artery out of said plurality of sensor elements based on a sphygmographic waveform detected with said pressure pulse wave sensor, a sphygmographic waveform value calculation unit calculating a characteristic value from the sphygmographic waveform detected with said selected sensor element, a distortion degree calculation unit calculating difference in distortion degree of sphygmographic waveforms detected with respective said sensor elements, based on a sphygmographic waveform detected with said selected sensor element and a sphygmographic waveform detected with at least one sensor element located at a predetermined distance from said selected sensor element, and an amplitude value correction unit correcting an amplitude value using said calculated difference in distortion degree, wherein said distortion degree calculation unit calculates a ratio of an amplitude of a sphygmographic waveform detected with said selected sensor element to an amplitude of a sphygmographic waveform detected with said at least one sensor element located at a predetermined distance from said selected element, as said difference in distortion degree.

* * * * *